US006679893B1

(12) United States Patent
Tran (10) Patent No.: US 6,679,893 B1
(45) Date of Patent: Jan. 20, 2004

(54) GRASPING DEVICE AND METHOD OF USE

(75) Inventor: Quang Q. Tran, Redwood City, CA (US)

(73) Assignee: Chestnut Medical Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/715,667

(22) Filed: Nov. 16, 2000

(51) Int. Cl.[7] .............................................. A61B 17/22
(52) U.S. Cl. ..................................................... 606/127
(58) Field of Search ................................ 606/127, 128, 606/159, 198, 200

(56) References Cited

U.S. PATENT DOCUMENTS

| | | | |
|---|---|---|---|
| 4,612,931 A | 9/1986 | Dormia | |
| 4,625,726 A | 12/1986 | Duthoy | |
| 4,807,626 A | * 2/1989 | McGirr | 606/127 |
| 4,873,978 A | 10/1989 | Ginsburg | |
| 4,909,789 A | 3/1990 | Taguchi et al. | |
| 5,064,428 A | 11/1991 | Cope et al. | |
| 5,300,086 A | 4/1994 | Gory et al. | |
| 5,330,482 A | 7/1994 | Gibbs et al. | |
| 5,387,219 A | 2/1995 | Rappe | |
| 5,688,234 A | 11/1997 | Frisbie | |
| 5,846,248 A | 12/1998 | Chu et al. | |
| 5,895,398 A | 4/1999 | Wensel et al. | |
| 5,908,435 A | 6/1999 | Samuels | |
| 5,916,235 A | 6/1999 | Guglielmi | |
| 5,944,728 A | 8/1999 | Bates | |
| 5,968,057 A | 10/1999 | Taheri | |
| 5,972,019 A | 10/1999 | Engelson et al. | |
| 6,013,086 A | 1/2000 | Ouchi et al. | |
| 6,027,520 A | 2/2000 | Tsugita et al. | |
| 6,066,158 A | 5/2000 | Engelson et al. | |
| 6,174,318 B1 | * 1/2001 | Bates et al. | 606/127 |
| 6,416,519 B1 | * 7/2002 | VanDusseldorp | 606/127 |
| 6,500,182 B2 | * 12/2002 | Foster | 606/127 |

FOREIGN PATENT DOCUMENTS

EP 0743 046 A1 11/1996

* cited by examiner

Primary Examiner—Peter Nerbun
(74) Attorney, Agent, or Firm—Banner & Witcoff, Ltd.

(57) ABSTRACT

The invention is directed to a grasping device and system and the method of using the device and system for capturing a thromboembolism and other objects or masses within a patient's body lumen, particularly from within a patient's cerebral blood vessels. The grasping device has an elongated core member with a grasping assembly of arms on the distal end of the core member which have an expanded and a contracted configuration. The expanded configuration permits the arms to surround an object such as a thrombus or clot and a contracted configuration to grasp or capture the object. The distal ends of the arms are provided with object grasping members such as one or more teeth to facilitate the capture and removal of the object. A delivery catheter and a shorter guide catheter aid in delivering the grasping device to the desired intravascular location within the patient.

71 Claims, 7 Drawing Sheets

GRASPING DEVICE AND METHOD OF USE

FIELD OF THE INVENTION

The invention is an intracorporeal device and method for grasping objects within a patient's body and withdrawing the grasped objects from the patient's body. More specifically, the intracorporeal device is a grasping device and system for removing an object such as thrombus from a patient's vasculature, particularly the cerebral vascular anatomy, where such an object may cause a debilitating stroke.

BACKGROUND

Several devices and methods have been previously disclosed for removing objects from different regions of the body. Some previous devices and methods, hereafter referred to as "grasping" devices, are intended for grasping or engaging an object where it resides in the body and removing it from that location. These grasping devices are designed to be delivered to the particular site where the target object resides in the body—the object is then engaged by the grasping device and removed from the body. More specific examples of grasping devices have been disclosed for specifically engaging and removing the following from respective body cavities or other locations: gall stones, foreign objects such as implanted medical devices e.g. "snares", and vascular occlusions such as occlusive thrombi. In one particular device that is disclosed for engaging and removing a calculus principally kidney stones, a grasping assembly includes a plurality of arms arranged in a circumferential pattern in order to capture a target stone to capture the target calculus between them. The device operates via a centrally located plunger that is adjustable longitudinally along proximal tapers of the arms in order to force their detached distal ends apart to open the array for placement around the kidney stone calculus.

Other previously disclosed devices and methods are designed to provide a filter for catching or trapping emboli flowing through a body lumen, such as a blood filter for providing a cage across a blood vessel that is designed to catch debris flowing along the blood vessel downstream from an intervention or other embolic event. Some such filtering devices and methods are intended for removing the caught calculi after it is trapped in the filter. For example, one such known device is a probe-like strainer device that is placed retrograde through a puncture wound in a femoral artery downstream from a peripheral angioplasty site in order to catch emboli flowing downstream from an angioplasty or atherectomy site as a filter. This device includes a plurality of tines that open within the femoral artery in cone shaped arrangement that is constructed specifically for catching emboli flowing into the filter, such as by either providing a sufficiently large number of tines or by providing lateral members extending between adjacent tines to form a web-like strainer structure.

More specific examples of filtering and grasping devices and associated methods targeting specific calculi and the like for removal from various region of the body are disclosed in the following U.S. Patent references:

U.S. Pat. No. 4,612,931 to Dormia; U.S. Pat. No. 4,625,726 to Duthoy; U.S. Pat. No. 4,873,978 to Ginsburg; U.S. Pat. No. 5,064,428 to Cope et al.; U.S. Pat. No. 5,300,086 to Gory et al.; U.S. Pat. No. 5,330,482 to Gibbs et at.; U.S. Pat. No. 5,387,219 to Rappe; U.S. Pat. No. 5,846,248 to Chu et al.; U.S. Pat. No. 5,895,398 to Wensel et al.; U.S. Pat. No. 5,908,435 to Samuels; U.S. Pat. No. 5,944,728 to Bates; U.S. Pat. No. 5,968,057 to Taheri; U.S. Pat. No. 5,972,019 to Engelson et al.; U.S. Pat. No. 6,013,086 to Ouchi et al.; and U.S. Pat. No. 6,027,520 to Tsugita et al.

Recent developments in medical technology and associated treatments have been focused on clearing or removing thromboembolisms or "blood clots" from the cervical and cerebral vasculature in order to treat thromboembolic stroke victims. Thromboembolic stroke is a life threatening condition that consists of arrested blood flow to a region of the brain due to a thromboembolisum blocking a blood vessel feeding that region. Such thrombi often originate in the left heart chambers, break free into the aorta and flow downstream into the cervical neck arteries e.g. carotid arteries, and then ultimately lodge into a narrowed vessel somewhere down the narrowing vascular tree of the cerebral arteries associated with the brain in the head. Once lodged, the thrombus occludes flow along the vessel downstream of the blockage, thus arresting blood flow to the downstream blood vessel and causing the stroke.

Several recent techniques have been disclosed for ablating or "breaking up" a thromboembolism at a cervical or cerebral occlusion location in order to treat stroke. According to one known technique, a standard guidewire, more commonly used to guide medical catheter devices to remote body spaces like a rail, is used to "Dotter" through and break up the occluding clot in order to clear it from the occlusive site. However, fragments of the clot then break free to flow to a downstream site, often still resulting in harmful stroke to other regions of brain tissue. Other more recently disclosed devices and methods are intended to ablate the clot with focused energy delivery, such as for example sonic or laser ablation. However, these techniques also carry the risk of stroking downstream brain tissue. In addition, several of these approaches are very expensive and require specialized hardware to operate the respective ablation catheters.

Several grasping device assemblies and methods have been disclosed specifically for removing thrombi from the cervical and cerebral vessels in order to treat thromboembolic stroke. However, many of these devices have grasping assemblies that are not well adopted for delivery to distal regions of the cerebral vessels where many thromboembolisms are known to cause a debilitating stroke. For example, such known devices are not well designed for delivery to distal cerebral vascular locations through standard cerebral vascular delivery catheters that typically have delivery lumens with very small inner diameters, such as for example through delivery catheters with inner diameters of about 0.042 inch or less, generally adapted to track over a guidewire with an outer diameter of about 0.032 inch or 0.035 inch, or through still smaller delivery catheters with inner diameters of about 0.022 inch, generally adapted to track over a 0.018 inch or less OD guidewire, or through the still smaller standard delivery catheters having inner diameters of about 0.018 inch or less, generally adapted to track over a 0.014 inch OD guidewire. In addition, many of these assemblies and associated methods may not be predictable or easy to operate when engaging and removing an offending blood clot from a cerebral vessel, and particularly from distal cerebral vessels.

Distal cerebral blood vessels typically have inner lumens less than 4 mm and are quite tortuous. For example they have a plurality of 180° bends with a radius of curvature not greater than about 2 cm with spacing between the bends being not greater than about 10 cm. Advancing instruments for therapeutic or diagnostic uses through such anatomy is difficult.

There is a present unmet need for devices for capturing and removing thromboembolisms and other objects from small tortuous body lumens such as distal cerebral vessels.

SUMMARY OF THE INVENTION

This invention is directed to an intracorporeal grasping device and system for capturing an object or mass such as a thromboembolic occlusion in a patient's vasculature and the method of such capturing and removal.

The grasping device has an elongated core member with proximal and distal core sections and a grasping assembly secured to the distal end of the elongated core member which has a plurality of arms circumferentially and preferably uniformly disposed about the longitudinal axis of the grasping device. The proximal ends of the arms are secured to the distal end of the elongated core member. The grasping assembly has contracted and expanded configurations. In the expanded configuration within a body lumen, the arms have distal sections which are spaced from and essentially parallel to the longitudinal axis of the elongated core member (e.g. ±5° from the longitudinal axis).

In one presently preferred embodiment of the invention, the grasping system includes a delivery catheter for delivery of the grasping device to the desired location within the patient's vasculature. The delivery catheter has proximal and distal core member sections, ports in the proximal and distal ends and an inner lumen extending within the delivery catheter to and in fluid communication with the ports. The inner lumen is configured to slidably receive the grasping device with the grasping assembly thereon in the contracted configuration. When the grasping assembly extends out the port in the distal end of the delivery catheter, it deploys to its expanded configuration with the distal portion of the arms spaced from and parallel to the longitudinal axis of the grasping device. The delivery catheter is shorter than the grasping device so that the proximal end of the grasping device extends out the proximal port of the delivery catheter when the grasping assembly on the device extends out the port in the distal end of the delivery catheter.

In the grasping procedure, the delivery catheter is advanced to a location within the patient's vasculature, or other body lumen, that is proximally adjacent to the object or mass to be grasped such as a thrombus or embolism. The grasping device is advanced within the delivery catheter until the assembly of the grasping device extends out the port in the distal end of the delivery catheter and deploys in the expanded configuration. The grasping device is further advanced so the distal arm sections extend around the periphery of the object or mass to be grasped. Once arms are properly positioned about the object or mass, the delivery catheter is distally advanced while the grasping device is held in place so that the distal end of the delivery catheter presses against the proximal arm sections of the grasping assembly forcing the arms of the assembly into the contracted or partially contracted configuration. The retaining or grasping elements on the distal ends of the distal arm sections are forced into the object or mass when the assembly is forced into the contracted configuration and thereby facilitates the grasping and subsequent removal of the object or mass.

The grasping system is predictable and easy to use in capturing and removing a thromboembolic occlusion, particularly from a cerebral vessel. Moreover, it is simple and inexpensive to make and use for the treatment of cerebral thromboembolic stroke.

One presently preferred embodiment of the invention includes a guide catheter in addition to the delivery catheter and a grasping device. The guide catheter has a guiding passageway extending between ports in the proximal and distal ends of the catheter and is adapted to be positioned within a vascular anatomy of the patient such that the distal port is located at a desired location such as at a cervical vessel and the proximal end portion of the guide catheter extends from a vascular access site, such as a femoral artery, with the proximal port located externally of the patient. The guide catheter is shorter than the delivery catheter and the inner lumen of the guide catheter is configured so that the delivery catheter can be slidably disposed within the guiding catheter inner lumen with the delivery catheter's distal end portion extended distally through the guide catheter's distal port with the delivery catheter distal port positioned at the cerebral vessel, and further such that the delivery catheter proximal port is located proximally of the guide catheter proximal port externally of the patient. In this manner the grasping device may be advanced through the inner lumen of the delivery catheter by the manipulation of the proximal end of the elongated core member which extends out of the proximal port of the delivery catheter. This also facilitates holding the proximal end of the grasping device and the distal advance of the delivery catheter when forcing the grasping assembly on the distal end of the elongated core member of the grasping device into a contracted configuration when capturing and withdrawing an object.

The grasping device and system of the invention are particularly suitable for grasping and removal of a cerebral thrombus and can be delivered to the desired location of a thromboembolism through neurovascular delivery catheters having an inner lumen with a diameter that is 0.042 inch (1.067 mm) or less, or even 0.022 inch or 0.018 inch (0.559 or 0.457 mm) or less, respectively.

Therefore, the invention is a medical device system and method for removing a thrombus from a location within a cerebral vessel associated with a brain of a patient, and includes the following embodiments, aspects, and further beneficial variations.

According to one further aspect of the invention, the system may include a guide member such as a conventional guidewire with a proximal end portion and a distal end portion that is adapted to be positioned at the location of the object to be removed. The guide member is adapted to be slidably disposed within the inner lumen of the delivery catheter so that the delivery catheter can track over the guide member in order to position the distal port of the delivery catheter immediately adjacent to the location of the object to be captured.

The system of the invention may also include an introducer with a proximal end portion with a proximal introducer bore associated with a hemostatic valve, a distal end portion with a distal introducer port, and an introducer passageway extending between the proximal and distal introducer ports. The distal end portion of the introducer is adapted to be positioned across the vascular access site with the distal introducer port within the patient's vasculature and with the proximal introducer port and hemostatic valve positioned externally of the patient. The guide catheter is adapted to be introduced into the vascular access site through the introducer passageway for positioning of the guide catheter distal end portion along the desired body lumen.

For cerebral use, the grasping device is about 135 to 175 cm long preferably at least 150 cm long.

The guide catheter and the, delivery catheter, are configured with respective lengths that are specially adapted for delivery of the grasping assembly to a distal region of a patient's vascular anatomy. In one regard, the guide catheter may be between about 90 and about 110 cm long, the delivery catheter may be between about 125 cm and about 160 cm long.

Each of the arms of the grasping assembly is adjustable with an applied force from the expanded configuration to a partially or completely contracted configuration, respectively. In one further beneficial variation, each arm is adjustable with force from the expanded configuration to the partially contracted and contracted configurations respectively, by pressing the distal end portion of the delivery catheter against the inclined proximal portion of the arms. Preferably the arms have an outwardly inclined proximal sections extending distally away from the distal end of the core wire at an angle with respect to the longitudinal axis. The inclination of the proximal sections allow for controllable adjustment of the positioning for the arm's distal end portion by advancing the outer delivery catheter along the inclined proximal sections.

The distal end portion of the arms terminate with an engaging element such as a tooth that is oriented radially inwardly toward the longitudinal axis. By adjusting the grasping assembly with the arms around the object from the expanded configuration to the contracted configuration, each grasping element is forced into the object to be removed.

The grasping assembly's arms may be arranged in a manner that maximizes the ability to grasp and remove the target object, but while minimizing the cross-section and overall size of the arm assembly within the delivery catheter and within the body lumen. More specifically, when the grasping assembly is in the expanded configuration at the location of the object to be grasped, the arms are arranged in such a manner that an embolism with an outer diameter that is equal to or less than ⅓ the inner diameter of the body lumen at the location may pass through the grasping assembly. In a further variation generally associated with larger arms or more arms, the plurality of arms in the expanded configuration is adopted to allow an object with an outer diameter that is equal to or less than ¼ the inner diameter of the body lumen at the location to pass through the grasping assembly.

The grasping assembly should have at least 3 arms arranged in a circumferential pattern about the longitudinal axis of the grasping device. Usually no more than 6 arms are needed. A presently preferred embodiment of the grasping device has four arms, which are uniformly spaced, e.g. at intervals of approximately 90° about the longitudinal axis of the device.

The elongated core member of the grasping device is preferably constructed at least in part of a metallic core wire. In one highly beneficial variation, a coil surrounds and is secured to the distal end of the metallic core wire. Preferably the coil is made from a metal and is sufficiently radiopaque to facilitate fluoroscopic observation. The elongated core member of the grasping device has enough stiffness to advance the arms of the grasping assembly in the expanded condition around the object to be grasped and the distal end portion of the elongated core member and the grasping assembly in the first condition are sized and flexible enough to be advanced through vascular anatomy not greater than about 4 mm in diameter and having at least two 180 degree bends with a radius of curvature not greater than about 2 cm and a spacing between bends not greater than about 10 cm. These dimensions are typical for cerebral arteries.

Each of the arms may be secured to the elongated core member of the grasping device at a location distally of the coil. The elongated core member of the grasping device should include a lubricious coating such as a fluoropolymer, e.g. Teflon® or suitable hydrophilic coating. The proximal core portion of the core wire has a uniform outer diameter and the distal core portion is more flexible than the proximal core section. The increased flexibility can be obtained by smaller transverse dimensions or the use of a more flexible material for the distal core section. The distal core portion is preferably tapered in the distal direction to smaller transverse dimensions. In another variation, the outer diameter of the proximal portion of the core wire is equal to or less than about 0.035 inch and the distal portion of the core wire has an outer diameter equal to or less than about 0.018 inch.

The distal core portion of the elongated core member is preferably at least 25% more flexible than the proximal core portion. The core member may have a shaped or shapeable distal end.

The system of the invention includes positioning a guide catheter, delivery catheter, and grasping device in particular locations within the anatomy of the patient in order to grasp the object from the location. More specifically, this method of use may includes positioning the guide catheter such that a distal guide port of the guide catheter is positioned at a location within the patient's vasculature and the proximal end portion of the guide catheter extends across a vascular access site with a proximal guide port of the inner lumen of the guide catheter positioned externally of the patient. The delivery catheter is positioned within the inner lumen of the guide catheter with a distal end portion of the delivery catheter extending distally through the distal guide port of the guide catheter with the distal delivery port of the delivery catheter at or proximal to the location within the patient's vasculature. The proximal end portion of the delivery catheter extends proximally through the proximal port of the guide catheter with a proximal delivery port of the inner lumen of the delivery catheter located externally of the inner lumen of the guide catheter and of the patient.

After grasping the object from the location, the delivery catheter and grasping device may be removed from the patient. The guide catheter may be removed from the patient while the grasping assembly and grasped object are located within the inner lumen of the guide catheter. An alternative variation includes removing the grasping assembly and engaged object from the patient proximally through the proximal guide port while the distal guide port is located within the body lumen.

The present invention provides a predictable and easy to use device and system for grasping an object such as a thromboembolic occlusion from a patients body lumen particularly from a cerebral blood vessel. These and other advantages of the invention become apparent from the following detailed description and the accompanying exemplary drawings.

DETAILED DESCRIPTION OF THE INVENTION

Figure 1:
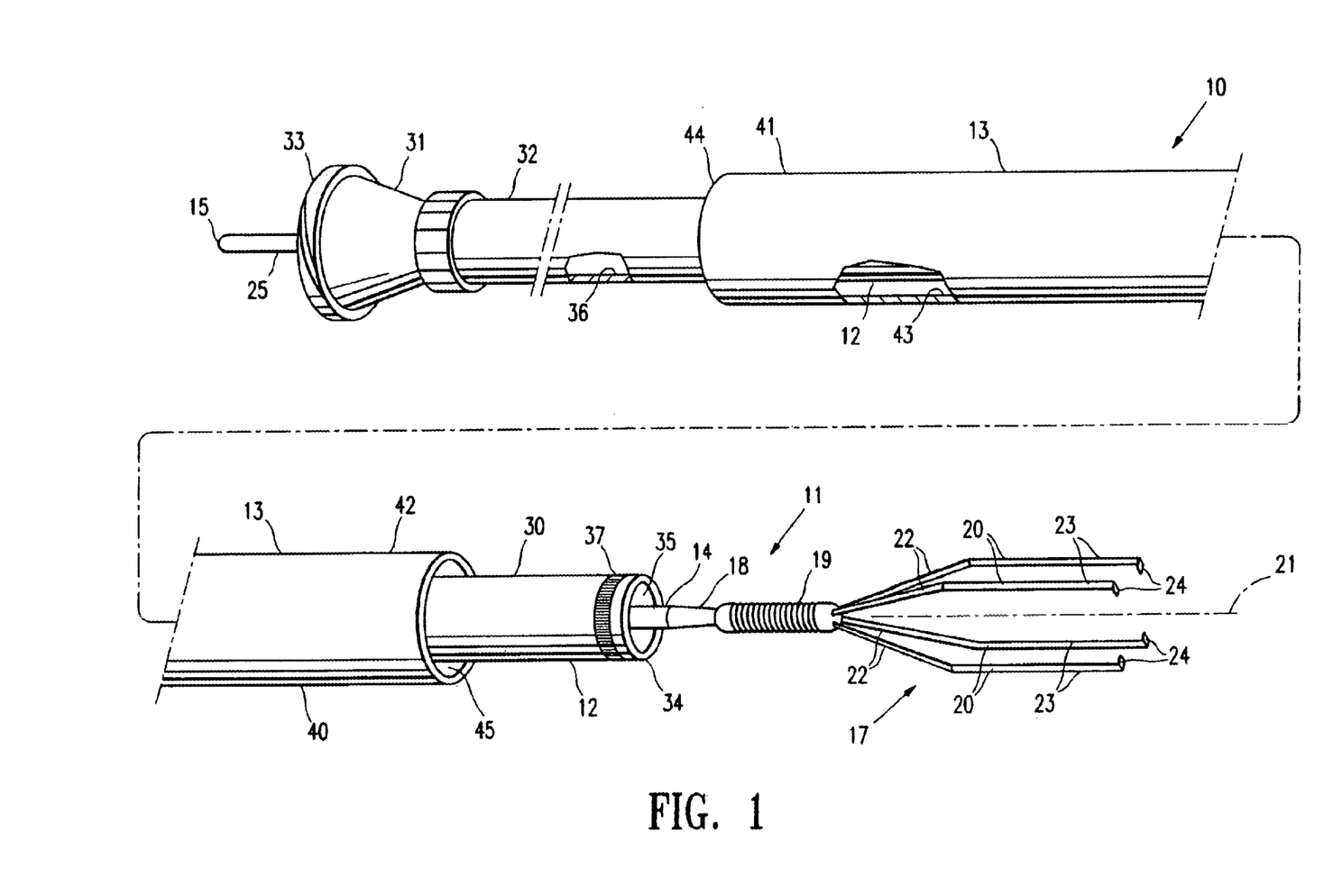
FIG. 1 is a schematic drawing showing a perspective view of an intracorporeal grasping system embodying features of the invention. The system includes a guide catheter, a delivery catheter, and a grasping device.

FIG. 1 schematically illustrates an intracorporeal grasping system 10 having features of the invention. The grasping system 10 depicted includes a grasping device 11, a delivery catheter 12 and a guide catheter 13. In some instances only the grasping device 11 and either the delivery catheter 12 or the guide catheter 13 are required, but not both.

Figures 2, 3, 4:
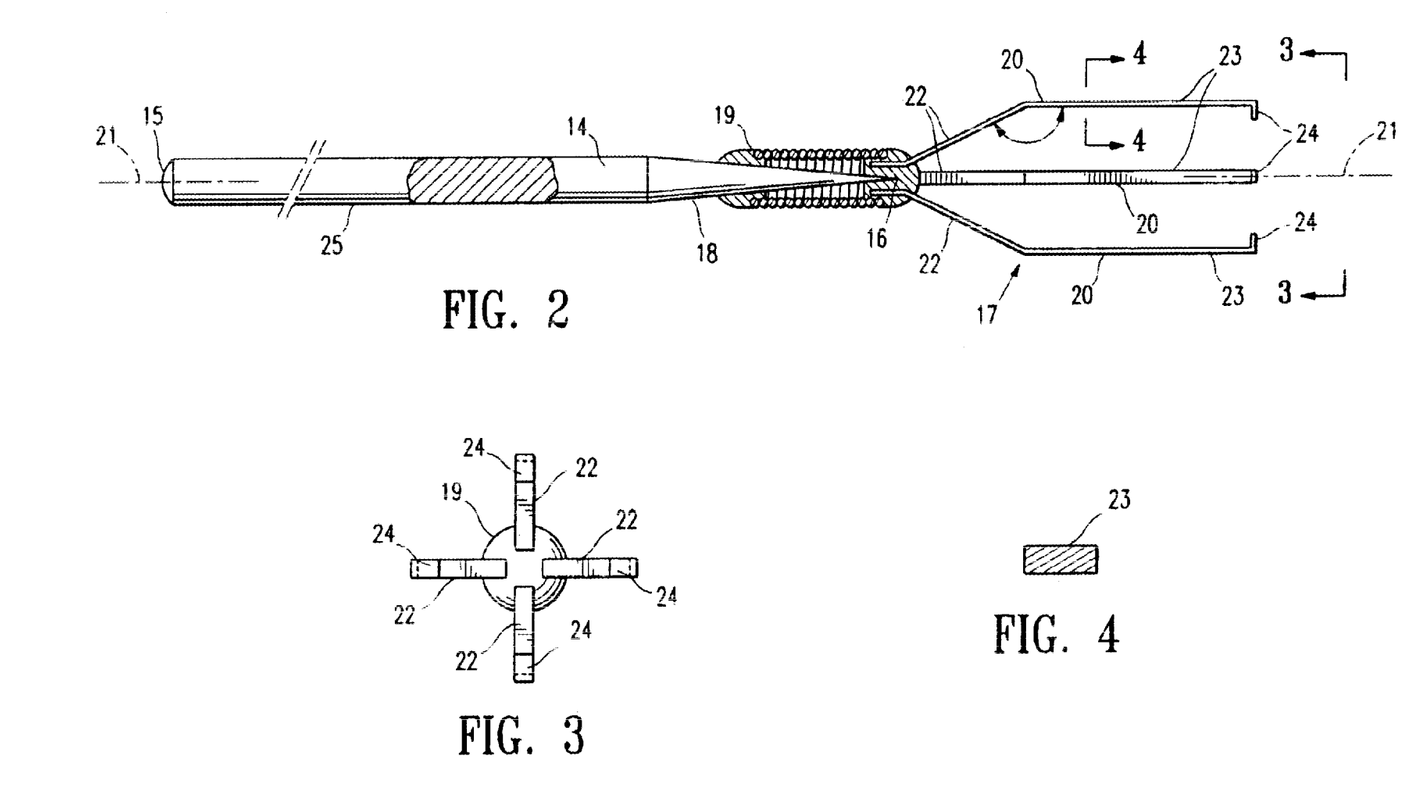
FIG. 2 is an elevational view, partially a center line longitudinal cross-sectional view, of the grasping device shown in FIG. 1.
FIG. 3 is an end view of the grasping device taken along the line 3—3 shown in FIG. 2.
FIG. 4 is a transverse cross-sectional view of a distal arm section of the grasping device shown in FIG. 2 taken along the line 4—4.

As shown in FIG. 1 and in greater detail in FIGS. 2–4, the grasping device 11 has an elongate core member 14 with a proximal end 15 and a distal end 16, a grasping assembly 17 secured to the distal end of the core member. The distal portion 18 of the core member 14 is preferably distally tapered as shown with a helical coil 19 disposed about and secured to the distal end 16 of the core member. The grasping assembly 17 has a plurality of arms 20 disposed about the longitudinal axis 21 of the device 11 with proximal arm sections 22 secured to the distal end 16 of the core member 14 and distal arm sections 23 which extend essentially parallel to the longitudinal axis 21 e.g. not more than 5° from a line parallel to longitudinal axis when the grasping assembly 17 is in an expanded configuration as shown. The distal arm sections 23 have inwardly extending, object engaging elements 24 at their distal ends. The bluntness of the object engaging element 17 provides a non-traumatic feature to the distal end of the arms 20. The proximal portion 25 of the grasping device 11 is usually of uniform outer diameter and is of sufficient length so that the proximal end 15 extends out of the delivery catheter 12 when the grasping assembly 17 extends out the distal end of the delivery catheter.

Figure 5:
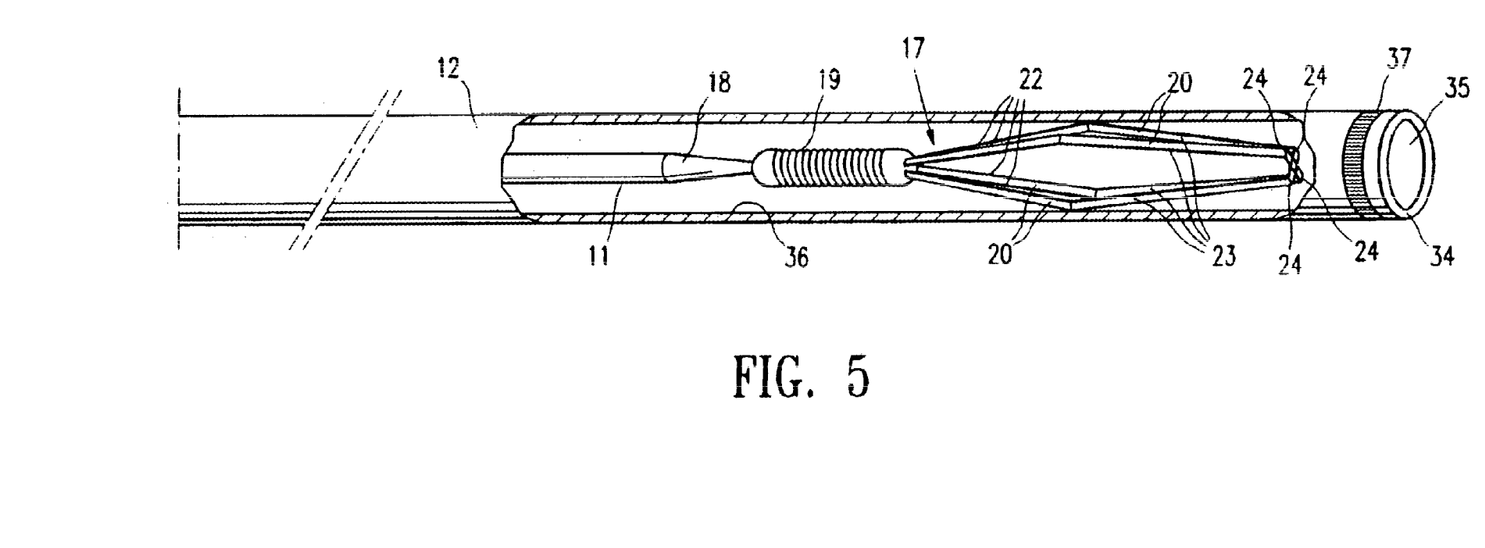
FIG. 5 shows a side elevational view, partially in section, of the grasping device shown in FIG. 2 in a closed configuration within the inner lumen of the delivery catheter.

As shown in FIG. 1 the delivery catheter 12 has a tubular body 30 with an adapter 31 on the proximal end 32, a port 33 in the adapter 31, a distal end 34, a port 35 in the distal end and an inner lumen 36 extending between and in fluid communication with proximal port 33 in the adapter 31 and the distal port 35. A radiopaque marker 37 is provided on the distal end 34 to facilitate fluoroscopic observation of the distal end of the delivery catheter 12 during a procedure within a patient's body, such as a thrombectomy. The inner lumen 36 is configured to slidably receive the grasping device 11 with the grasping assembly 17 in the contracted configuration as shown in FIG. 5. The adapter 31 is preferably provided with a hemostatic valve (not shown).

Delivery catheter 12 is generally constructed to track over a conventional guidewire beyond the guide catheter 13 in the cervical anatomy and into the cerebral vessels associated with the brain and may also be chosen according to several standard, "microcatheter" designs that are generally available. Accordingly, delivery catheter 12 has a length that is at least 125 cm long, and more particularly may be between about 125 cm and about 175 cm long, Typically the delivery catheter 12 is about 155 cm long. The inner lumen 36 of the delivery catheter generally has an inner diameter between about 0.01 inch and about 0.08 inch (0.25–2.03 mm). Commercially available microcatheters which may be suitable for use as delivery catheters include the TURBOTRAKER™ catheter, which is available from Target Therapeutics, Inc., and the RAPIDTRANSIT™ catheter available from Cordis Endovascular Corporation.

Also shown in FIG. 1 is guide catheter 13 has a tubular body 40, a proximal end 41, a distal end 42, and an inner lumen 43 extending between a proximal port 44 in the proximal end and a distal port 45 in the distal end of the guide catheter. The proximal end 41 of guide catheter 13 may be provided with an adapter (not shown) having a hemostatic valve. Guide catheter 13 is generally constructed to bridge between a femoral artery access site and a cervical region of the carotid or vertebral artery and may be chosen according to several standard designs that are generally available. Accordingly, guide catheter 13 is generally at least 85 cm long, and more particularly may be between about 95 cm and about 105 cm long. Further to conventional and available designs, the inner lumen 43 of guide catheter 13 generally has an inner diameter that is between about 0.038 inch and 0.090 inch (0.88–2.29 mm), and more particularly may be between about 0.052 inch and about 0.065 inch (1.32–1.65 mm).

Grasping device 11 is configured to slidably fit within the inner lumen 36 of delivery catheter 12. For procedures involving distal locations of thromboembolic neurovascular occlusions, the grasping device 11 is configured to be delivered through the inner lumen 36 of the delivery catheter 12 with a diameter that is equal to or less than about 0.042 inches (1.07 mm), preferably less than about 0.022 inches (0.559 mm). In the case of use in a more distal, tortuous, and smaller vessel anatomy, configuration for delivery through an delivery catheter inner lumen less than 0.018 inch (0.457 mm) may be required. For most neurovascular occlusions, the grasping device 11 is about 135 to about 300 cm long, and more particularly may be about 150 cm to about 200 cm long. Typically, the grasping device 11 is about 175 cm long and is adapted to be used in a delivery catheter 12 that is about 150 cm long.

The elongated core member 14 of the grasping device 11 is similar to core members found in conventional guidewires and generally is a solid elongated member formed of a high strength material such as stainless steel, superelastic nickel-titanium alloy, cobalt-chromium-molybdenum alloys such as MP35N and Elgiloy or other material having suitable strength, stiffness, and other attributes for allowing percutaneous transluminal manipulation of the grasping device 11 as described herein.

Referencing FIG. 2, the distal portion 18 of core member 14 is shown as being continuously tapered from the larger outer diameter of the proximal portion 25 to a reduced outer diameter at the distal end 16 to provide increased flexibility over the proximal portion. However, the taper may be stepped to various regions of diameter reduction in the distal portion 18. The tapered distal portion 18 may be of different lengths depending upon the intended intracorporeal location of use, but generally will be about 5 cm to about 70 cm in length, typically about 45 cm in length.

The outer diameter of the proximal portion 25 of core member 14 should be selected for slidable advancement within the inner lumen of the delivery catheter. Generally, the proximal portion 25 is about 0.007 inches to about 0.040 inch (0.18–1.02 mm) in diameter, and preferably about 0.008 to about 0.038 inch (0.203–0.97 mm) in diameter. An outer lubricous coating (not shown) may be provided on the exterior of the core member 14 at least along distal portion 18. Suitable coatings include fluoropolymers such as polytetrafluoroethylene (Teflon®) or hydrophilic materials. The outer diameter of the distal portion 18 of core member 14 may be about 0.001 inch to about 0.018 inch (0.025–0.457 mm) in maximum transverse cross section. The most distal part of the distal portion may be flattened as done in conventional vascular guide wires.

The coil 19 is disposed about the distal portion 25 of core member 14 and may be secured to the distal portion by soldering e.g. with silver or gold solder. Other methods of securing the coil 19 include brazing, welding, adhesives, mechanical connections or other suitable techniques. The coil 19 as shown is a helically wound wire of preferably radiopaque metal, such as for example platinum. However, the coil 19 may be formed of coiled ribbon material. Coil 19 generally has an overall length in the wound condition of about 1 cm to about 60 cm, and an outer diameter essentially the same as the proximal portion 25 of core member 14 e.g. about 0.007 inch to about 0.040 inch (0.18–1.02 mm). The wire or ribbon forming the coil generally has a short transverse dimension of about 0.001 to about 0.003 inch (0.025–0.076 mm). A stacked or expanded coil configuration may be utilized depending upon the location of use contemplated.

The grasping assembly 17 has a plurality of arms 20 which are disposed about the longitudinal axis 21 and each of arms 20 has a proximal arm section 22 secured to the distal end 16 of the core member 14. The proximal arm sections 22 are inclined from the distal end 16 of the core member 14 and are integrally with the distal arm sections 14. The inclined proximal arm sections 22 function to aid in placing the plurality of arms 20 of the grasping assembly 17 into a contracted or partially contracted configuration about the longitudinal axis 21 by the force applied to the inclined sections by advancement of the distal end of the delivery catheter 12, as is further developed below, and have lengths selected to provide the desired radial spacing between the distal arm sections 23 and as a result the spacing from the longitudinal axis 21 for the contracted configuration of the grasping assembly 17. The inclined proximal arm sections 22 may be straight as shown or they may be curved to provide the desired expansion or contraction of the distal arm sections 23 of the grasping assembly 17. The proximal arm sections 22 are generally about 1 mm to about 30 mm in length and preferably about 1.5 mm to about 4 mm in length. The proximal arm sections 22 and the distal arm sections 23 join at an angle in the expanded configuration as shown in FIG. 2 of about 110° to about 160°, preferably about 120° to about 150°.

The distal arm sections 23 have free ends which include one or more object grasping members 24 oriented radially inwardly toward the longitudinal axis 21. The object grasping members 24 are constructed to engage an object, e.g. thrombus, and facilitate its removal from the body. The object engaging members 24 may be inclined proximally or distally at an angle from a plane which is perpendicular to the longitudinal axis 21. A proximal orientation of the object engaging member 24 may aid the proximal withdrawal of certain engaged objects such as clots during removal. An additional benefit from the object engaging members 24 is that they allow the grasping assembly to be advanced within delicate cerebral arteries in an expanded configuration with minimal risk of perforating or otherwise damaging the blood vessel wall.

The grasping assembly 17 generally has a plurality of arms 20 positioned about the longitudinal axis 21, and preferably has from three to six arms uniformly disposed about the longitudinal axis. Generally, no advantage is found with more than six arms The presently preferred embodiment has four arms uniformly positioned about the longitudinal axis 21. The distal arm sections 23 may have different lengths for different specific intended procedures. However, for most uses the distal arm sections 23 are about 0.1 mm to about 50 mm long, preferably about 5 to about 40 mm. Moreover, the object engaging members 24 at the distal ends of the distal arm sections 23 may also have varied lengths depending upon their intended use, although in general, they will usually be about 0.5 mm to about 9 mm in length, preferably about 0.5 mm and about 1 mm in length.

Opposing pairs of arms 20 and the proximal and distal arm sections 22 and 23 respectively of opposing pairs of arms 20 may be of different lengths in order to grasp an object at different locations along its length.

Figure 6:
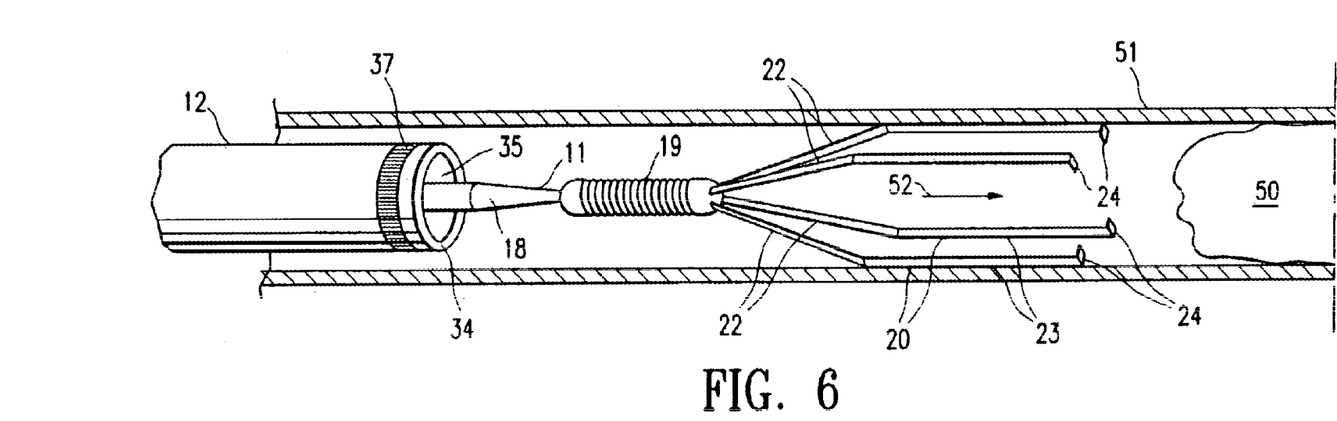
FIG. 6 depicts the grasping device disposed within the delivery catheter with the grasping assembly of the device extending out the port in the distal end of the delivery catheter into a body lumen adjacent to a thrombus and being in an expanded configuration therein.

The transverse dimensions of the grasping assembly 17 with the distal arm sections 23 in an expanded configuration should be chosen to be approximately the same transverse dimension, from slightly smaller to slightly larger than the inner transverse dimensions of the body lumen at the location where the object is to be grasped as shown in FIG. 6. However, in general the transverse dimensions of the grasping assembly in the expanded configuration is about 1 mm to about 9 mm, and preferably about 2 mm to about 4 mm in order to treat distal cerebral vessels as will be further developed below.

Arms 20 are shown in the figures as flat ribbons. For most uses these ribbons have a generally rectangular transverse cross section with a long transverse dimension of about 0.001 inch to about 0.09 inch (0.025–2.29 mm), and a short transverse dimension of about 0.00025 inch to about 0.01 inch (0.006–0.25 mm). These dimensions maximize the strength of the arms 20 for use in engaging and manipulating the target object such as a thrombus, while minimizing the transverse cross-section of the arms 20 with respect to longitudinal axis 21 which allows the grasping assembly 17 in a contracted configuration to fit into the inner lumen 36 of delivery catheter 12. Alternatively the arms 20 may be formed of wires with circular transverse cross sections having diameters equivalent to the short transverse dimensions of the ribboned arms discussed above, namely about 0.00025 inch to about 0.01 inch (0.006–0.25 mm).

Figure 7:
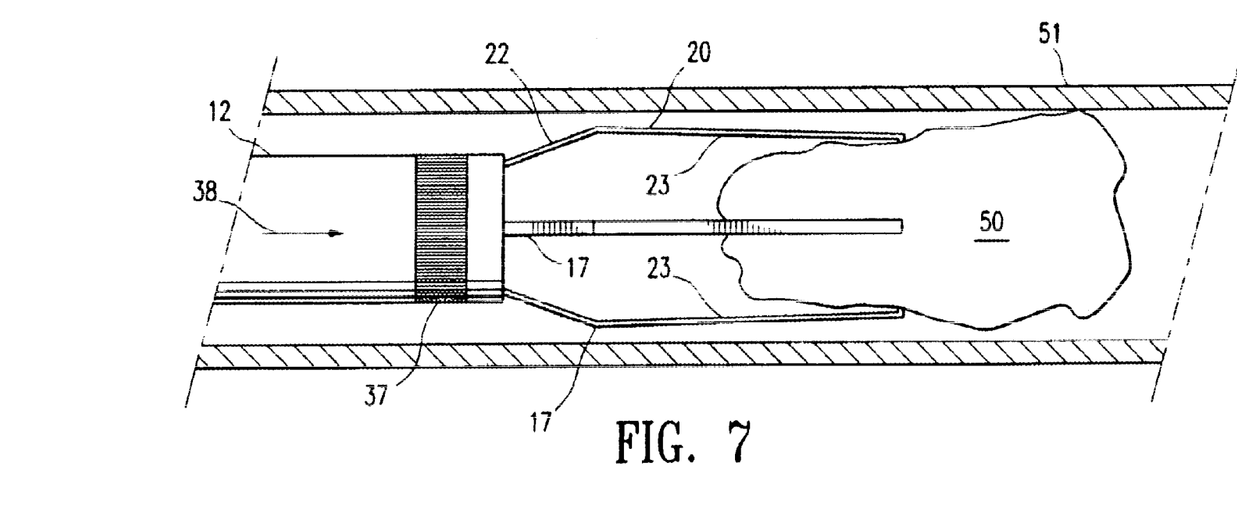
FIG. 7 illustrates an elevational view of the grasping device within the delivery catheter having the grasping assembly on the distal end of the device being in a partially contracted configuration about a thromboembolism.

Grasping assembly 17 is adjustable between three principal configurations, namely, completely contracted or nearly so as shown in FIG. 5 to facilitate disposition within the inner lumen 36 of delivery catheter 12, completely expanded or nearly so as shown in FIGS. 1, 2 and 6 to facilitate advancement of the expanded grasping assembly 17 within the body lumen about the object to be captured and partially contracted to hold onto or capture the object as shown in FIG. 7. Grasping assembly 17 is shown in FIGS. 1, 2 and 6 in the expanded configuration which is characterized by each of the arms 20 in a completely expanded position and the distal arm sections 23 being generally parallel or nearly parallel to longitudinal axis 21, which in a preferred embodiment is the relaxed memory state for the arms 20.

Grasping assembly 17 is adjustable from the expanded configuration as is shown in FIG. 6 to the contracted or partially contracted configuration by the application of force against the inclined proximal arm sections 22 by advancing the distal end 35 of the delivery catheter 12 as shown by the arrow 38 in FIG. 7 against the inclined proximal arm sections.

Arms 20 may be constructed of various materials having suitable strength, elasticity and memory for use in engaging and removing an object such as thrombus from a body lumen, particularly a cerebral vessel. However, arms 20 are generally constructed from a metal which may be for example platinum (or alloys thereof), stainless steel, superelastic nickel-titanium alloy, or high strength cobalt-chromium-molybdenum alloys. Platinum or alloys thereof are preferred because they provide a particular beneficial combination of a non-traumatic distal tip for the arms 20 and radiopacity for fluoroscopic observation of the arms in an intracorporeal procedure.

More specific features of the use of the device and system of the invention in capturing and removing thromboembolic occlusions from the distal cerebral vessels are described below.

Figure 8:
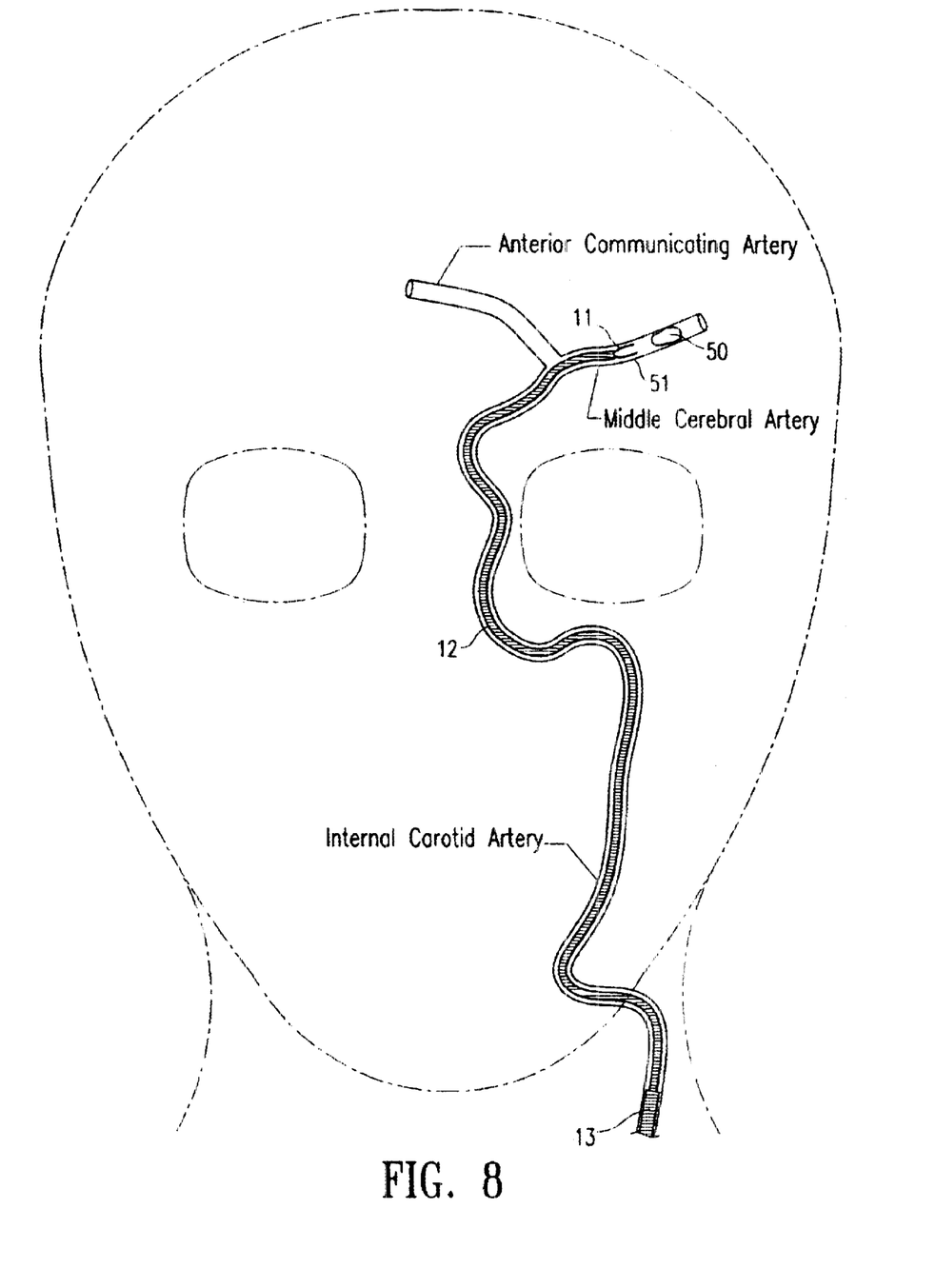
FIG. 8 is a schematic illustration of the grasping system shown in FIG. 1 operatively disposed in a left side internal carotid artery location in position to perform a thrombectomy procedure within the middle cerebral artery.

First, an access site is prepared as either a puncture wound (i.e. Seldinger technique) or as a surgical cut-down, typically in the femoral artery although in rare circumstances vascular access may be made at other peripheral vessels such as a brachial artery. A conventional introducer (not shown) may be used to provide hemostatic access at the access site via an incorporated hemostatic valve. Guide catheter 13 is than advanced through the introducer until distal end 42 is positioned with distal port 45 at a region of a cervical vessel 50, thereby providing transluminal access to the cervical vascular tree as shown in FIG. 8. Delivery catheter 12 is advanced through the inner lumen 43 of guide catheter 13 and out the distal port 45 thereof until the distal end 34 of the delivery catheter is positioned adjacent to the thromboembolism 50 located in the middle cerebral artery 51. In the case where the distal location of the thromboembolism is beyond a bifurcated vessel or otherwise tortuous cerebral vessels, the delivery catheter 12 may be advanced over a conventional guide wire (not shown). Once the delivery catheter 12 is positioned adjacent to the thromboembolism 50, the guide wire is removed from the patient and is then replaced with grasping device 11. Grasping device 11 is advanced through the inner lumen 36 of the delivery catheter in the contracted configuration as shown in FIG. 5, until it exits through distal port 35 into the blood vessel 51 where the grasping assembly 17 self-adjusts to the expanded configuration with arms 20 in a radially expanded position. Grasping assembly 17 is then advanced, as indicated by the arrow 52, in the expanded configuration distally so that arms 20 advance around the thromboembolism 50 as shown in FIG. 6. Then, delivery catheter 12 is advanced distally to press against proximal arm sections 22 to force distal arm sections 23 to rotate radially inwardly to a partially contracted configuration so that the object engaging members 24 engage the thromboembolism 50 as shown in FIG. 7. Thereafter, the grasping device 11, delivery catheter 12, and thromboembolism 50 may be removed from the location and further from the body, either through guide catheter 13 or together in combination with guide catheter.

Figure 9:
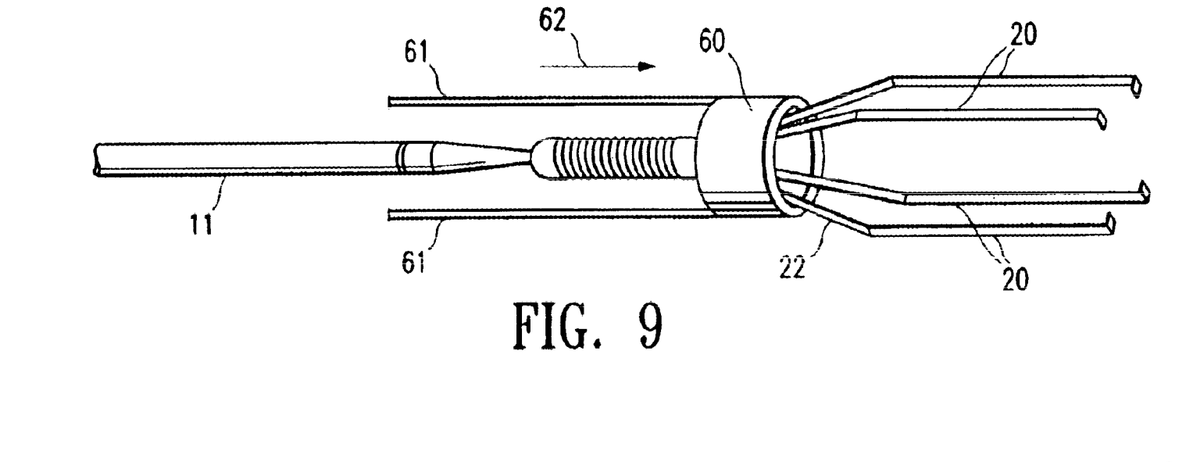
FIG. 9 is a schematic illustration of an alternative grasping device having other mechanism to change the grasping assembly from an expanded configuration to a contracted or partially contracted configuration.

A variety of other mechanisms may be employed to change the grasping assembly 17 from an expanded configuration to a contracted configuration. For example, in FIG. 9 the grasping system has a collar or short sheath 60 for placing the grasping arms 20 in a contracted configuration. The collar or sheath 60 is distally advanced against the proximal art sections 22 of the grasping assembly 17 by a plurality of struts 61, as indicated by arrow 62, which have proximal ends extending out the proximal end of a delivery or guiding catheter (not shown) to facilitate such distal movement. The collar presses against the proximal arm sections 22 in the same manner as the distal portion of the delivery catheter 12 in the previously discussed embodiment.

Figure 10:
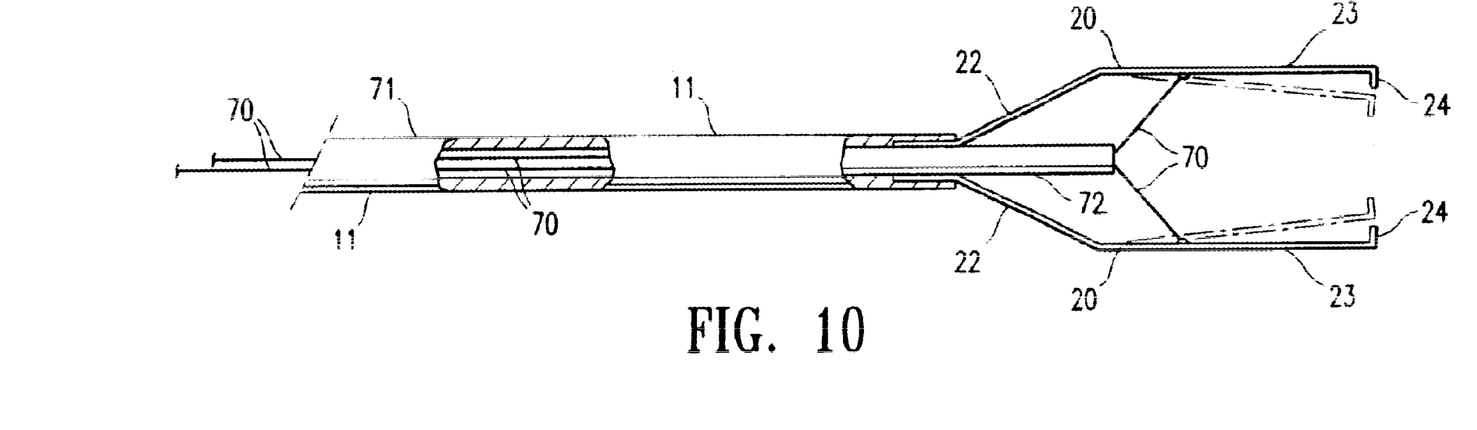
FIG. 10 is a schematic illustration of another alternative grasping device having other mechanism to change from an expanded configuration to a closed or partially closed configuration.

Another mechanism is shown in FIG. 10 wherein the grasping system has a plurality of wires or strands 70 secured to the inner surface of the arms 20 such as attached to the distal arm sections 23 which when pulled to apply a tensile force to the arms pull the arms into a contracted configuration as shown in phantom. The wires or strands may extend through a lumen provided in the core member, i.e. the core member may be a hypotube 71 as shown. Note that the distal portion 72 of the hollow core member extends into the interior of the grasping assembly for a greater degree of leverage when pulling the arms 20 into a contracted configuration.

Figure 11:
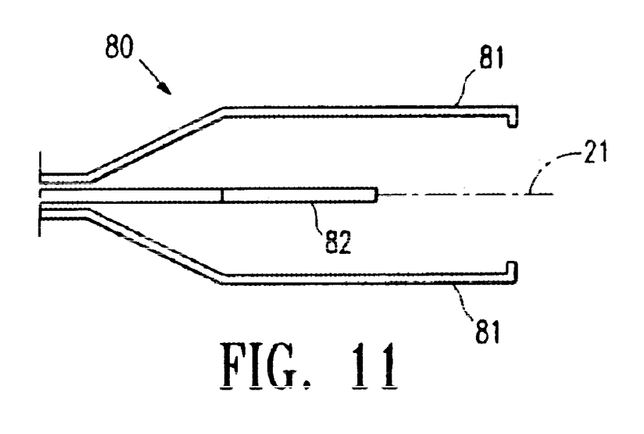
FIG. 11 is a schematic illustration of a grasping assembly having one pair of opposed arms of different lengths than another pair of opposed arms.

FIG. 11 depicts a grasping assembly 80 which has a first pair of opposing arms 81 which are of different lengths than a second pair of opposing arms 82. One of the opposing arms 82 is not shown in the drawing because it is behind the arm 82 shown. The off-set pairs of arms 81 and 82 grasp an object along its length and can facilitate removal of difficult to remove objects.

Figure 12A:
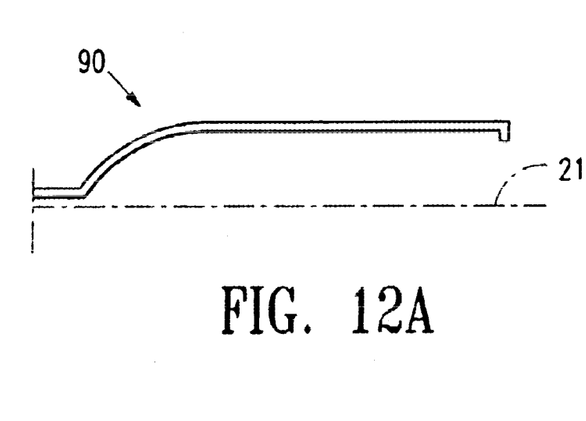
FIGS. 12A, 12B and 12C illustrate proximal arm sections of various shapes.
Figure 12B:
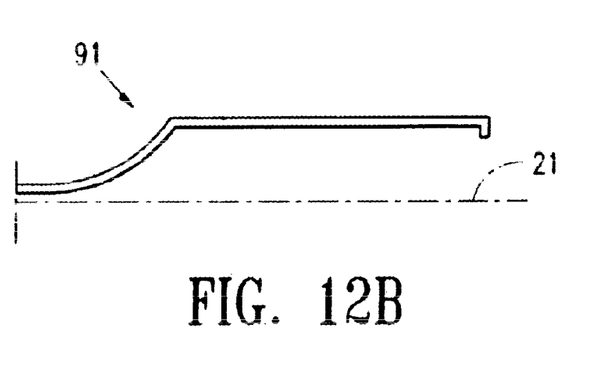
Figure 12C:
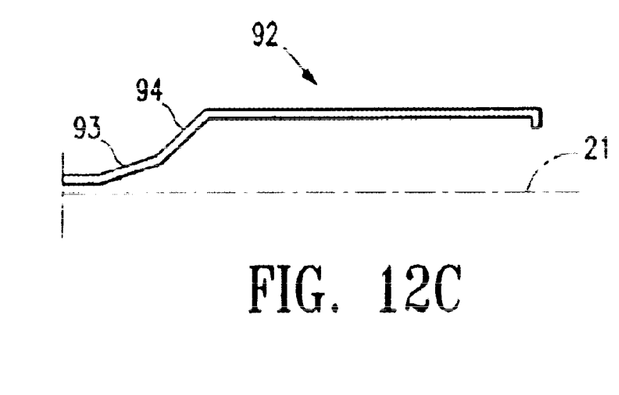

FIGS. 12A, 12B and 12C illustrate proximal arm sections 90, 91 and 92 having a variety of shapes. The proximal arm section 90 curves outwardly, proximal arm section 91 curves inwardly and proximal arm section 92 has two straight portions 93 and 94 at slightly different angles with respect to the longitudinal axis.

While the embodiments just described are believed to be well suited for engaging and removing various objects from various body spaces, the primary basis underlying many of the beneficial features herein described are for the purpose of accessing distal, tortuous cerebral vessels for removal of thromboembolism in the treatment of strokes, as previously described above.

The particular embodiments shown and described by reference to the figures should not be considered limiting to the invention, and obvious modifications and combinations of features and embodiments according to this disclosure may be made by one of ordinary skill without departing from the scope of this invention. Moreover, use of the terms "device", "member", "element" or "mechanism" herein or in the appending claims shall not invoke the provisions of 35 U.S.C. §112(6) unless specific reference is made to "means" followed by an intended function. Similarly, reference to a portion or portions of a method or process herein or in the appending claims shall not invoke the provisions of 35 U.S.C. §112(6) unless specific reference is made to a "step" followed by an intended function.

What is claimed is:

1. An intracorporeal grasping device having a longitudinal axis, comprising:
   a. an elongated core member having proximal and distal end portions, said elongated core member being tapered alone at least a portion of its distal end portion such that the diameter of a portion of said elongated core member intermediate said proximal and distal end portions is greater than the diameter of said tapered portion of said distal end portion; and
   b. a grasping assembly on the distal end of the elongated core member having a plurality of arms disposed about the longitudinal axis of the device and having an expanded and contracted configuration, with arms of the grasping assembly having proximal sections secured to the distal end of the elongated core member and distal sections which have free distal ends configured to grasp an object and which in the expanded configuration are essentially parallel to the longitudinal axis of the device.

2. The intracorporeal grasping device of claim 1 wherein the distal end portion of the elongated core member is more flexible than the proximal end portion.

3. The intracorporeal grasping device of claim 2 wherein the distal portion of the core member is at least in part more than 25% more flexible than the proximal portion of the core member.

4. The intracorporeal grasping device of claim 1 wherein the elongated core member has a flexible body disposed about and secured to the tapered portion of said distal end portion.

5. The intracorporeal grasping device of claim 2 wherein the distal end portion of said core is formed of a first material, the proximal end portion of said core is formed of a second material, said first material being more flexible than said second material.

6. The intracorporeal grasping device of claim 1 wherein the arms of the grasping assembly are uniformly disposed about the longitudinal axis.

7. The intracorporeal grasping device of claim 1 wherein at least three arms are disposed about the longitudinal axis.

8. The intracorporeal grasping device of claim 1 wherein 4 to 8 arms are disposed about the longitudinal axis.

9. The intracorporeal grasping device of claim 1 wherein the distal arm sections have lengths of about 0.1 to about 50 mm.

10. The intracorporeal grasping device of claim 1 wherein the distal arm sections have lengths of about 5 to about 35 mm.

11. The intracorporeal grasping device, of claim 1 wherein the proximal arm sections have lengths of about 1 to about 30 mm.

12. The intracorporeal grasping device of claim 1 wherein the proximal arm sections have lengths of about 5 to about 20 mm.

13. The intracorporeal grasping device of claim 1 wherein the proximal arm sections incline outwardly from the distal end of the elongated core member when the grasping assembly is in an expanded configuration.

14. The intracorporeal grasping device of claim 1 wherein the proximal and distal arm sections join at an angle between about 110° and about 160° when the grasping assembly is in the expanded configuration.

15. The intracorporeal grasping device of claim 1 wherein the proximal and distal arm sections join at an angle between about 120° and about 150° when the grasping assembly is in the expanded configuration.

16. The intracorporeal grasping device of claim 1 wherein the grasping assembly has one pair of opposing arms having a first length and a second pair of opposing arms having a second length greater than the first length.

17. The intracorporeal grasping device of claim 16 wherein the proximal arm sections of the second pair of opposing arms are at least 0.5 mm greater in length than the proximal arm sections of the first pair of opposing arms.

18. The intracorporeal grasping device of claim 16 wherein the distal arm sections of the second pair of opposing arms are at least 0.5 mm greater in length than the distal arm sections of the first pair of opposing arms.

19. The intracorporeal grasping device of claim 1 wherein the distal ends of the distal arm sections have object grasping elements extending inwardly toward the longitudinal axis.

20. The intracorporeal grasping device of claim 19 wherein the object grasping elements are elongated teeth.

21. The intracorporeal grasping device of claim 19 wherein the object grasping elements are shorter than the distal arm sections.

22. The intracorporeal grasping device of claim 19 wherein the object engaging elements are about 0.1 to about 5 mm in length.

23. The intracorporeal grasping device of claim 1 wherein the proximal arm sections have proximal ends which are secured to the distal end portion of the elongated core member.

24. The intracorporeal grasping device of claim 20 wherein the proximal ends of the proximal arm sections are secured to the elongated core member to facilitate the assembly having expanded and contracted configurations.

25. The intracorporeal grasping device of claim 1 wherein the grasping assembly has an expanded configuration with a maximum transverse dimension of about 0.5 to about 10 mm.

26. The intracorporeal grasping device of claim 1 wherein the grasping assembly has an expanded configuration with a maximum transverse dimension of about 2 to about 9 mm.

27. The intracorporeal grasping device of claim 1 wherein the proximal arm sections are at least in part curved.

28. The intracorporeal grasping device of claim 1 wherein the proximal arm sections have a first straight portion inclined at a first angle with respect to the longitudinal axis and a second straight portion distal to the first straight portion at an angle with respect to the longitudinal axis greater than the angle of the first straight portion.

29. An intraluminal grasping system, comprising:
   a. an elongated delivery catheter having a distal end, a port in the distal end, a proximal end, a port in the proximal end and an inner lumen which is in fluid communication with the ports in the proximal and distal ends of the delivery catheter; and
   b. the grasping device of claim 1 slidably disposed within the inner lumen of the elongated delivery catheter.

30. The intraluminal grasping system of claim 29 wherein the grasping device is longer than the delivery catheter.

31. The intraluminal grasping system of claim 30 wherein the grasping device has a length such that the grasping assembly thereof extends out the port in the distal end of the delivery catheter while a proximal portion of the core member of the grasping device extends out of the proximal end of the delivery catheter.

32. A grasping system for procedures in tortuous intravascular locations, comprising:
   a. an elongated guide catheter having proximal end, a port in the proximal end, a distal end, a port in the distal end and an inner lumen extending therein which is in fluid communication with the ports in the proximal and distal ends of the guide catheter b. an elongated delivery catheter which is longer than the guide catheter, which is slidably disposed within the inner lumen of the guide catheter and which has a proximal end, a port in the proximal end, a distal end, a port in the distal end, and an inner lumen extending therein in fluid communication with the ports in the proximal and distal ends of the delivery catheter; and c. the grasping device of claim 1 slidably disposed within the inner lumen of the elongated delivery catheter.

33. The system of claim 32 wherein the grasping device is longer than the delivery catheter.

34. The system of claim 32 wherein the plurality of arms have a contracted configuration which has a maximum transverse cross section sufficiently small so that the grasping assembly on the distal end of the grasping device may be slidably advanced within the lumen of the delivery catheter.

35. The system of claim 32 wherein the grasping assembly in the expanded configuration is adapted to be distally advanced within a patient's blood vessel and so that the distal arm sections of the grasping assembly will be distally advanced along at least a portion of a cerebral blood vessel to surround an object therein to be captured.

36. The system of claim 32, wherein the grasping device is at least about 150 cm long.

37. The system of claim 32, wherein the guide catheter is about 90 cm to about 135 cm long; the delivery catheter is about 125 cm to about 175 cm long; and the grasping device is about 135 cm to about 300 cm long.

38. The system of claim 32, wherein the lumen of the delivery catheter has a diameter not greater than about 0.042 inches.

39. The system of claim 32, wherein the lumen of the delivery catheter has a diameter not greater than about 0.022 inches.

40. The system of claim 32, wherein the lumen of the delivery catheter has a diameter not greater than about 0.018 inches.

41. The system of claim 32, wherein each arm is adjustable from the expanded configuration to a contracted configuration by the application of force to the proximal arm sections thereof.

42. The system of claim 41, wherein a force is applied to the proximal arm sections by pressing the distal end of the delivery catheter against the proximal arm sections of the arms.

43. The system of claim 32, wherein the arms terminate distally with an object grasping member that is oriented radially inwardly toward the longitudinal axis, so that by adjusting the grasping assembly with the arms around the object from the expanded configuration to a contracted configuration, the object grasping members on the distal arm sections are forced into the object.

44. The system of claim 32, wherein in the contracted configurations, the plurality of arms of the grasping assembly are configured to allow an object with a maximum transverse dimension that is not greater than about $\frac{1}{3}$ the inner diameter of the expanded configuration to pass through the grasping assembly.

45. The system of claim 32, wherein in the contracted configuration, the plurality of arms are configured to allow an object with a maximum transverse dimension that is not greater than about $\frac{1}{4}$ the inner diameter of the expanded configuration to pass through the grasping assembly.

46. An elongated grasping system having a longitudinal axis for capturing and removing a thrombus from a location within a patient's blood vessel, comprising:

a. a grasping device having an elongate core member with a proximal end portion and a distal end portion, said elongated core member being tapered along at least a portion of its distal end portion such that the diameter of a portion of said elongated core member intermediate said proximal and distal end portions is greater than the diameter of said tapered portion of said distal end portion, and having a grasping assembly secured to the distal end portion of the core member with a plurality of arms disposed about the longitudinal axis, each arm having an expanded and contracted configuration, a proximal section inclined outwardly in an expanded configuration and a distal section that extends distally from the proximal section and having a free distal end with an inwardly oriented thrombus grasping member; and b. a means to change the configuration of the arms of the grasping assembly from an expanded configuration to a contracted configuration.

47. The system of claim 46, wherein the grasping assembly has at least three arms.

48. The system of claim 46, wherein the grasping assembly has from four to six arms.

49. The system of claim 46 wherein the arms are uniformly spaced about longitudinal axis.

50. The system of claim 46, wherein in the contracted configuration the plurality of arms of the grasping assembly are configured to allow an embolism with an outer diameter that is equal to or less than about $\frac{1}{3}$ the inner diameter of the expanded configuration of the grasping assembly to pass through the arms of the grasping assembly.

51. The system of claim 46, wherein in the contracted configuration the plurality of arms of the grasping assembly are configured to allow an embolism with an outer diameter that is equal to or less than about $\frac{1}{4}$ the inner diameter of the expanded configuration to pass through the arms of the grasping assembly.

52. The system of claim 46 wherein the means to change the arms of the grasping assembly from an expanded configuration to a contracted configuration applies a distally oriented force to the inclined proximal arm sections of the grasping assembly.

53. The system of claim 52 wherein the means to apply a distally oriented force to the inclined proximal arm sections of the grasping assembly is an elongated catheter that is slidably mounted over the grasping device.

54. The system of claim 52 wherein the means to apply a distally oriented force to the inclined proximal arm sections of the grasping assembly is a relatively short sheath that is slidably mounted over the grasping device and which has a plurality of struts secured to the sheath to advance the sheath over the grasping device.

55. The system of claim 46 wherein the means to change the arms of the grasping assembly from an expanded configuration to a contracted configuration applies an inwardly oriented tensile force to the arms of the grasping assembly.

56. The system of claim 55 wherein the means to apply an inwardly oriented tensile force to the arms of the grasping assembly are strands secured to an inner surface of the arms.

57. The system of claim 46 wherein the arms of the grasping assembly have distal ends with inwardly projecting thrombus grasping members.

58. An elongated grasping system for capturing and removing a thrombus from a location within a patient's cerebral blood vessel and having a longitudinal axis, comprising:

a. a grasping device having an elongate core member with a proximal end portion and a distal end portion more flexible at least in part than the proximal end portion, said elongated core member being tapered alone at least a portion of its distal end portion such that the diameter of a portion of said elongated core member intermediate said proximal and distal end portions is greater than the diameter of said tapered portion of said distal end portion, and having a grasping assembly secured to the distal end portion which has a plurality of arms disposed about the longitudinal axis, which has an expanded and contracted configuration and which has proximal arm sections inclined outwardly when the assembly is in an expanded configuration and distal arm sections that extend distally from the proximal arm sections and that have free distal ends with inwardly oriented thrombus grasping elements; and b. a delivery catheter having a proximal end, a port in the proximal end, a distal end, a port in the distal end and an inner lumen which extends between and in fluid communication with the ports in the proximal and distal ends and which is configured to slidably receive the grasping device; and c. the grasping device and the delivery catheter having distal portions which are sufficiently flexible to be advanced together through the patient's cerebral blood vessel to a location adjacent to the thrombus.

59. The system of claim 58, wherein a distal portion of the grasping device including the tapered distal portion of the elongate core member and the grasping assembly are adapted to be advanced through a cerebral blood vessel having an inner diameter not greater than about 4 millimeters and having at least two bends of at least 180° with a radius of curvature not greater than about 2 cm and a spacing between bends not greater than about 10 cm.

60. A method for capturing a thrombus within a cerebral blood vessel of a patient, comprising:

a. positioning a guide catheter within the vasculature of the patient so that a distal port of the guide catheter is positioned within a cervical region associated with the cerebral blood vessel, and a proximal port of the guide catheter is positioned externally of the patient;

b. positioning a delivery catheter within an inner lumen of the guide catheter and distally advancing the delivery catheter within the lumen until a distal portion of the delivery catheter extends distally through the distal port of the guide catheter and a distal port of the delivery catheter is proximally adjacent to the thrombus in the cerebral blood vessel while a proximal portion of the delivery catheter extends proximally through the proximal port of the guide catheter with a proximal port of the delivery catheter being external of the guide catheter and of the patient;

c. advancing the grasping device of claim 1 that is longer than the delivery catheter through the inner lumen of the delivery catheter with the grasping assembly in a contracted configuration until the grasping assembly extends out the port in the distal end of the delivery catheter into the cerebral blood vessel, where the grasping assembly expands into an expanded configuration;

d. further advancing the grasping device until the arms of the grasping assembly at least partially surround the thrombus within the cerebral vessel; and e. while the arms are positioned around the thrombus, adjusting the grasping assembly from the open condition to a contracted configuration presses the object grasping elements on the distal arm sections into the thrombus, thereby capturing the thrombus.

61. The method of claim 60 including withdrawing the grasping assembly with the captured thrombus from the cerebral blood vessel.

62. The method of claim 60, further comprising the steps of:

a. before the delivery catheter is positioned within the guide catheter, advancing a guide wire through the inner lumen of the guide catheter until a distal extremity of the guide wire extends out the distal port of the guiding catheter;

b. mounting the distal portion of the delivery catheter over a proximal extremity of the guidewire which extends out the proximal end of the guiding catheter;

c. advancing the delivery catheter through the inner lumen of the guide catheter over the guide wire until the distal end of the delivery catheter extends into the cerebral blood vessel and is proximally adjacent to the thrombus therein;

d. withdrawing the guide wire from the delivery catheter; and e. advancing the grasping device through the inner lumen of the delivery catheter to grasp the thrombus.

63. The method of claim 60, wherein the arms of the grasping assembly are adjusted from the expanded configuration to a contracted configuration by distally advancing the delivery catheter so the distal end thereof presses against the proximal arm sections causing the object grasping members on the distal arm sections to be pressed into the thrombus, thereby capturing the thrombus.

64. The method of claim 63, further comprising:

after capturing the thrombus, withdrawing the delivery catheter and grasping device at least until the grasping assembly and captured thrombus are positioned within the inner lumen of the guide catheter.

65. The method of claim 64, further comprising:

removing the guide catheter, the delivery catheter and the grasping device with captured thrombus from the patient while the delivery catheter grasping assembly and thrombus are located within the inner lumen of the guide catheter.

66. The method of claim 64, further comprising:

removing the grasping device and captured thrombus from the patient proximally through the proximal port of the guide catheter while the distal port of the guide catheter remains within the cervical region of the cerebral blood vessel.

67. A method for removing a thrombus from a blood vessel of a patient, comprising:

a. providing the grasping device of claim 1;

b. advancing the grasping device within the patient's vasculature and with the grasping assembly of the grasping device in a contracted configuration until the grasping assembly of the device is proximally adjacent to the thrombus in the blood vessel;

c. expanding the grasping assembly into an expanded configuration;

d. advancing the grasping device with the grasping assembly in an expanded configuration until the arms of the assembly surround at least a portion of the thrombus;

e. adjusting the grasping assembly from the expanded configuration to a contracted configuration to capture the thrombus; and d. removing the grasping device and the captured thrombus from the patient.

68. An intracorporeal grasping device having a longitudinal axis, comprising:

a. an elongated core member having a proximal end portion and a distal end portion which is at least in part more flexible than the proximal end portion, said elongated core member being tapered along at least a portion of its distal end portion such that the diameter of a portion of said elongated core member intermediate said proximal and distal end portions is greater than the diameter of said tapered portion of said distal end portion;

b. a grasping assembly mounted on the distal end portion of said elongated core member, said grasping assembly having a plurality of arms disposed about the longitudinal axis of the device and having an expanded and contracted configuration, with arms of the grasping assembly having proximal arm sections secured to the distal end portion of said core member and distal arm sections which have free distal ends configured to grasp an object and which in the expanded configuration are essentially parallel to the longitudinal axis of the device.

69. The intracorporeal grasping device of claim 68 wherein the distal portion of the core member is at least in part more than 25% more flexible than the proximal portion of the core member.

70. The intracorporeal grasping device, of claim 68 wherein the elongated core member has a flexible body disposed about and secured to the tapered distal end portion.

71. The intracorporeal grasping device of claim 68 wherein the distal end portion of said core member is formed of a first flexible material, the proximal end portion of said core member is formed of a second material, and wherein said first material is more flexible than said second material.

* * * * *